United States Patent
Matson

[11] Patent Number: 6,093,413
[45] Date of Patent: Jul. 25, 2000

[54] ARTICLE FOR RELEASE OF REPELLENTS AND INSECTICIDES

[76] Inventor: Clifford D. Matson, 827 Spruce St., Junction City, Oreg. 97448

[21] Appl. No.: 09/161,016

[22] Filed: Sep. 25, 1998

Related U.S. Application Data

[63] Continuation-in-part of application No. 08/774,957, Dec. 27, 1996, abandoned.

[51] Int. Cl.[7] ............................................ A01N 25/34
[52] U.S. Cl. ..................... 424/403; 424/405; 424/406; 424/407; 424/411; 424/413; 424/DIG. 10; 514/919
[58] Field of Search ............................ 428/321.1, 343, 428/455, 456; 106/164.11; 424/406, 408, 403, 411, 407, 413, DIG. 7, DIG. 10; 514/919, 918

[56] References Cited

U.S. PATENT DOCUMENTS

| | | | |
|---|---|---|---|
| 1,608,243 | 11/1926 | Schavoir | 117/148 |
| 2,317,328 | 4/1943 | Kinney | 117/148 |
| 5,455,043 | 10/1995 | Fischel-Ghodsian | 424/448 |
| 5,480,851 | 1/1996 | Cramp et al. | 504/239 |

*Primary Examiner*—Neil S. Levy
*Attorney, Agent, or Firm*—James D. Givanan, Jr.

[57] ABSTRACT

An article for placement on a surface and having a carrier body of cork in which a quantity of a repellent or insecticidal agent is stored for vaporization over a duration. The carrier body is provided with an electrostatic retainer or an adhesive strip for article rentention on a surface. Repellent or insecticidal agents include those from pyrethrum or an extract from seeds of the neem tree or diazanon, the latter when the article is used outdoors.

6 Claims, 1 Drawing Sheet

ARTICLE FOR RELEASE OF REPELLENTS AND INSECTICIDES

This is a continuation-in-part of application Ser. No. 08/774,957, filed Dec. 27, 1996, filed by the present inventor, now abandonded.

BACKGROUND OF THE INVENTION

The present invention concerns an article bearing a quantity of insect repellent or pesticide and attachable to a surface area.

U.S. Pat. Nos. 5,071,704 and 5,455,043 (a continuation-in-part thereof) disclose the use of an adhesive on a laminate article having an insecticide bearing component. The articles disclosed in both of the above patents have several laminae including an adhesive member, an impermeable backing member, a reservoir member, a diffusion rate limiting member and a decorative outer layer. The compound carried within the polymeric reservoir member of the laminate is mentioned as being a perfume or fragrance or an insect repellent with diffusion of same controlled by a porous limiting membrane. The reservoir layer or member was disclosed in U.S. Pat. No. 5,071,704 as being of a cellulose nature or a polymer gel or porous polypropylene. Both of the foregoing patents disclose laminate structures with several layers or laminae.

U.S. Pat. No. 4,849,279 discloses an insect-repellent assembly utilizing a carrier member of activated carbon fibers which carries an insect repellent. The carrier member may be paper containing activated carbon fibers. Various methods for applying the insect repellent to a carrier body include dipping, spraying, coating (utilizing rolls) with insecticide or insect-repellent agent suitable for repelling cockroaches.

U.S. Pat. No. 5,364,636 discloses an animal repelling article having sustained release capability with various suggested agents directed toward achieving sustained release of the repellent.

U.S. Pat. No. 2,317,328 discloses the application of an adhesive to the surface of articles of cork composition.

U.S. Pat. No. 1,608,248 discloses the use of granulated cork as a constituent of sheet material.

SUMMARY OF THE PRESENT INVENTION

The present invention is embodied within the combination of cork as a carrier and a pesticide or repellent.

Cork which has a highly desireable closed cellular nature as approximately half the volume of a cork body are spaces defined by elastic membranes with a minimum of voids therebetween. The unique cellular structure of cork enables a relatively large amount of pesticide or repellent to be stored therein for release at a desired rate without reliance on a laminae for controlling diffusion. Provision is made for securement of the pesticide or repellent bearing carrier to a supporting surface which provision may include an electrostatic or adhesive member. Suitable pesticides include pyrethrum and neem-seed extract permitting the use of the present article indoors as well as out-of-doors. For outdoor use only, Diazanon may be utilized.

DETAILED DESCRIPTION OF THE PREFERRED EMBODIMENTS OF THE INVENTION

Figure 1:
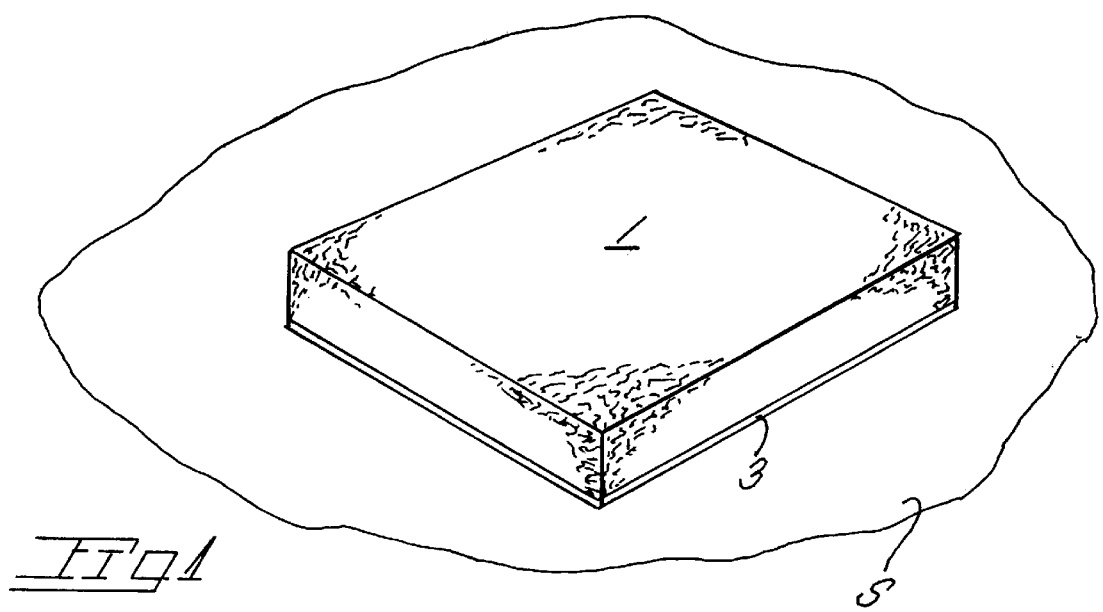
FIG. 1 is a perspective view of the present article embodying the invention.
Figure 2:
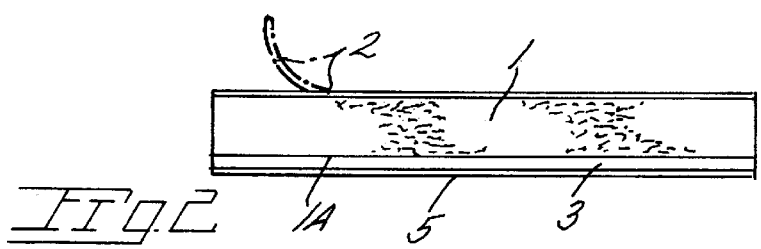
FIGS. 2 and 3 are side elevational views of different embodiments of the present article.
Figure 3:
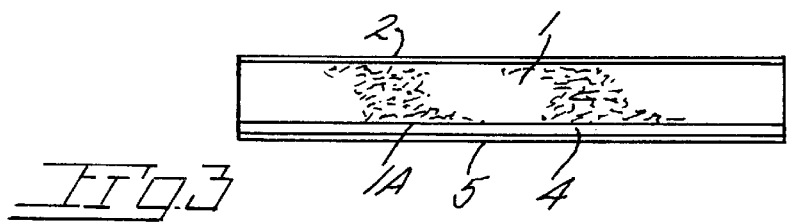

The present article includes a carrier at reference numeral 1 which is preferably of a size for inconspicuous use about a dwelling or other structure.

Carrier 1 is of cork from the phellem of the cork oak and which material is, by nature, tough and spongy. It is cellular having membrane defined spaces constituting approximately one-half the volume of the carrier. The membranes are elastic and are normally resistant to penetration by certain liquids but permeable by strong acid and alkali solutions.

Commonly, cork is processed for various uses such as e.g., flooring, bottle stoppers, bulletin boards, insulative and sound absorbent panels. Such uses may include granulation of the cork and subsequent combining of the particles under pressure with a binder. A suitable size and shape of the cork carrier for present purposes is one having a high surface area to depth ratio, e.g., the three dimensional shape of a patch having a thickness of one quarter of an inch and one inch square.

A removable impermeable barrier or cover is at 2 for removal at time of use to prevent dispersal onto the user's hands.

For retention of carrier 1 in place on a surface area S of a dwelling or other building or structure, adhesive means at 3 are provided in place on a carrier surface 1A. It has been determined that suitable means may be of an electrostatic nature, as for example, the application of a spray coating which, in effect, provides suitable adherence for article attachment to most any surface. An alternative means may be the use of an adhesive strip as at 4 which may be of the double sided type with a tear away or peelable protective cover at 5.

When carrier 1 is for use indoors for repelling insects indigenous to North America, a suitable combination of pesticides preferred for application to carrier 1 is as follows:

| Azadirachtin | .045% |
| Permethrin | 1.250% |
| Inert ingredients | 98.705% | with the amounts present, per cc of cork, being:

| Azadirachtin | .048 mg (+ or − 10 percent) |
| Permethrin | .185 mg (+ or − 10 percent) |

Azadirachtin is an extract from the seeds of the neem tree and is sold under the trademark NATURAL GUARD and manufactured by UPS, a Coop Gardening Group of Bonham, Tex.

Permethrin is marketed under the trademark SPECTRACIDE by the Spectrum Group, a Division of United Industries Corp., of St. Louis, Mo.

An insecticide marketed under the registered trademark MARGOSAN-O is neem-based and approved by the U.S. Environmental Protection Agency for certain uses. In one embodiment of the invention ten drops or so of MARGOSAN-O provides an adequate amount of insecticide when applied to a cork patch of the above noted dimensions and is effective for a period of weeks. The neem-based insecticide has found acceptance in commercial greenhouses and has been approved for use against insects or pests on food crops.

A patch may be treated solely with SPECTRACIDE and is specifically effective against cockroaches.

For outdoor use only, the present carrier of cork material has been satisfactorily used when treated with diazanon.

While I have shown but a few embodiments of the invention, it will be apparent to those skilled in the art that the invention may be embodied still otherwise without departing from the spirit and scope of the invention.

Having thus described the invention, what is desired to be secured by a Letters Patent is:

1. An article for release of an insect repellent or insecticidal agent effective over a duration of weeks for placement on a surface and comprising, a body of cork of three dimensional shape and having membrane defined internal spaces for receiving the repellent or agent and serving as a carrier for same, an insect repellent or insecticidal agent in said spaces, and means on said body for attaching said body to the surface.

2. The article claimed in claim 1 wherein said body is of granular composition and includes a binder.

3. The article claimed in claim 1 wherein said body is of granulated cork compressed into a three dimensional shape.

4. The article claimed in claim 1 wherein said means is an adhesive.

5. The article claimed in claim 1 wherein said body is of patch configuration having a surface dimension greater than its depth by a factor of 3–5.

6. The article claimed in claim 4 wherein said adhesive is of an electrostatic nature.

* * * * *